(12) United States Patent
Fenchel et al.

(10) Patent No.: US 8,638,095 B2
(45) Date of Patent: Jan. 28, 2014

(54) CORRECTION OF TRUNCATIONS IN MR IMAGING

(75) Inventors: Matthias Fenchel, Erlangen (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 607 days.

(21) Appl. No.: 12/893,140

(22) Filed: Sep. 29, 2010

(65) Prior Publication Data

US 2011/0080168 A1 Apr. 7, 2011

(30) Foreign Application Priority Data

Oct. 5, 2009 (DE) .......................... 10 2009 048 302

(51) Int. Cl.
*G01V 3/00* (2006.01)

(52) U.S. Cl.
USPC ........................................................ 324/309

(58) Field of Classification Search
USPC ................................................ 324/300–322
See application file for complete search history.

(56) References Cited

U.S. PATENT DOCUMENTS

| 7,444,011 | B2 * | 10/2008 | Pan et al. ........................ | 382/131 |
| 7,680,240 | B2 * | 3/2010 | Manjeshwar et al. ............. | 378/4 |
| 7,920,670 | B2 * | 4/2011 | Hugg et al. ........................ | 378/4 |
| 8,121,245 | B2 * | 2/2012 | Pan et al. ........................... | 378/2 |
| 8,326,054 | B2 * | 12/2012 | Chen et al. ..................... | 382/232 |
| 2009/0232377 | A1 | 9/2009 | Fahimian | |
| 2012/0275673 | A1 * | 11/2012 | Star-Lack et al. ............. | 382/131 |

OTHER PUBLICATIONS

Fabiana Crepaldi et al.: "Activity and Attenuation Reconstruction of Positron Emission Tomography Using Emission Data Only Via Maximum Likelihood and Iterative Data Refinement", IEEE Transactions on Nuclear Science, vol. 54, No. 1, Feb. 2007,; Others; 2007.
A comparison of models used as alternative magnetic resonance image reconstruction methods M.R. Smith and S.T. Nichols Department of Electrical Engineering, The University of Calgary p. 173 to 183: Others.
Data extrapolation for truncation artifact removal R.T. Constable and R.M. Henkelman Departmment of Medical Biophysiys, University of toronto, 500 Sherbourne Street, Toronto, Canada M4X 1K9 p. 108 to 118; Others.
Gaspar Delso et al.: "Impact of limited MR field-of-view in simultaneous PET/MR acquisition"; The Journal of Nuclear Medicine, 2008; 49; 162P; http://jnumedmtg.snmjournals.org/cgi/content/meeting_abstract/49/MeetingAbstracts_1/162P-b; Others; 2008.

(Continued)

*Primary Examiner* — Dixomara Vargas
(74) *Attorney, Agent, or Firm* — Harness, Dickey & Pierce, P.L.C.

(57) ABSTRACT

A method is disclosed for correction of truncations of a magnetic resonance image of an object under examination in the reconstruction of image data from raw data. In at least one embodiment, the method includes determining a number of one-dimensional projections of imaged field of view in the Radon space from the raw data in order to obtain a projection profile; checking each projection profile for whether the projection profile exhibits a truncation; if the respective checked projection profile exhibits a truncation, expanding the projection profile for correcting the truncation in that the projection profile is extrapolated in accordance with a predetermined extrapolation model in the area in which it exhibits the truncation; and reconstructing image data based on the expanded projection profiles in which the truncation of the image of the object under examination is corrected.

39 Claims, 9 Drawing Sheets

(56) References Cited

OTHER PUBLICATIONS

J. Nuyts et al: "Simultaneous maximum a posteriori reconstruction of attenuation and activity distributions from emmission sinograms", IEEE Trans. Med. Imag., vol. 18, No. 5, May 1999, pp. 393-403; Others; 1999.

Andrei V. Bronnikov: "Reconstruction of Attenuation Map Using Discrete Consistency Conditions", IEEE Transactions on Medical Imaging, vol. 19, No. 5, May 2000, p. 451-462; Others; 2000.

Accurate Reconstruction in PR-MRI despite Truncated Data J.K Barral, H.H. Wu, G.E. Gold, N.J. Pelc, J.M. Pauly and D.G. Nishimura Electrical Engineering, Stanford University USA; Others.

Suppression of MRI Truncation Artifacts Using Total Variation Constrained Data Extrapolation Kai Tobias Block, Martin Uecker and Jens Frahm Biomedizinische NMR Forschungs GmbH p. 1 to 8; Others.

Towards quantitative PET/MRI: a review of MR-based attenuation correction techniques Matthias Hofmann—Bernd Pichler—Bernhard Schölkopf—Thomas Beyer; Others.

\* cited by examiner

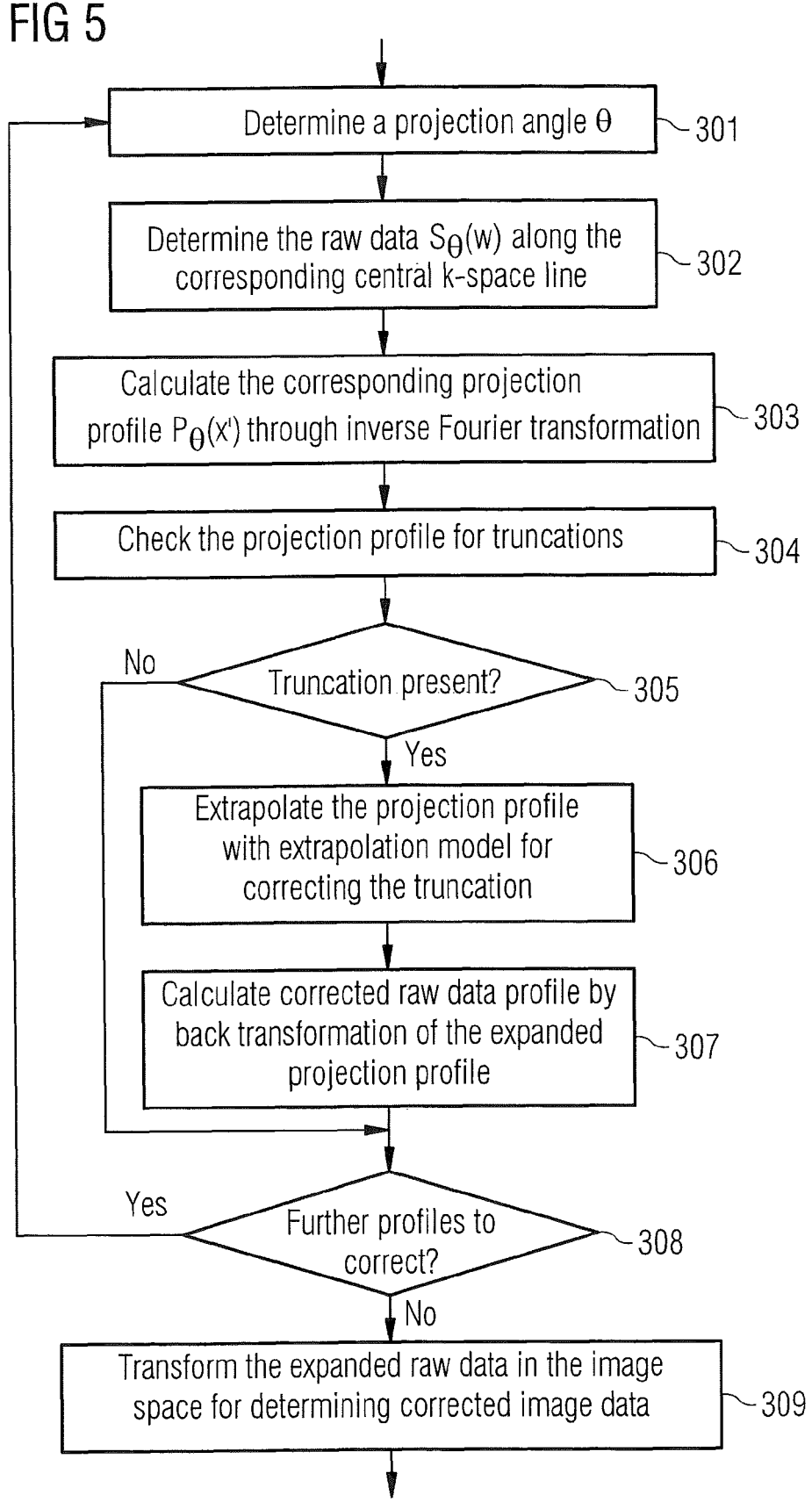

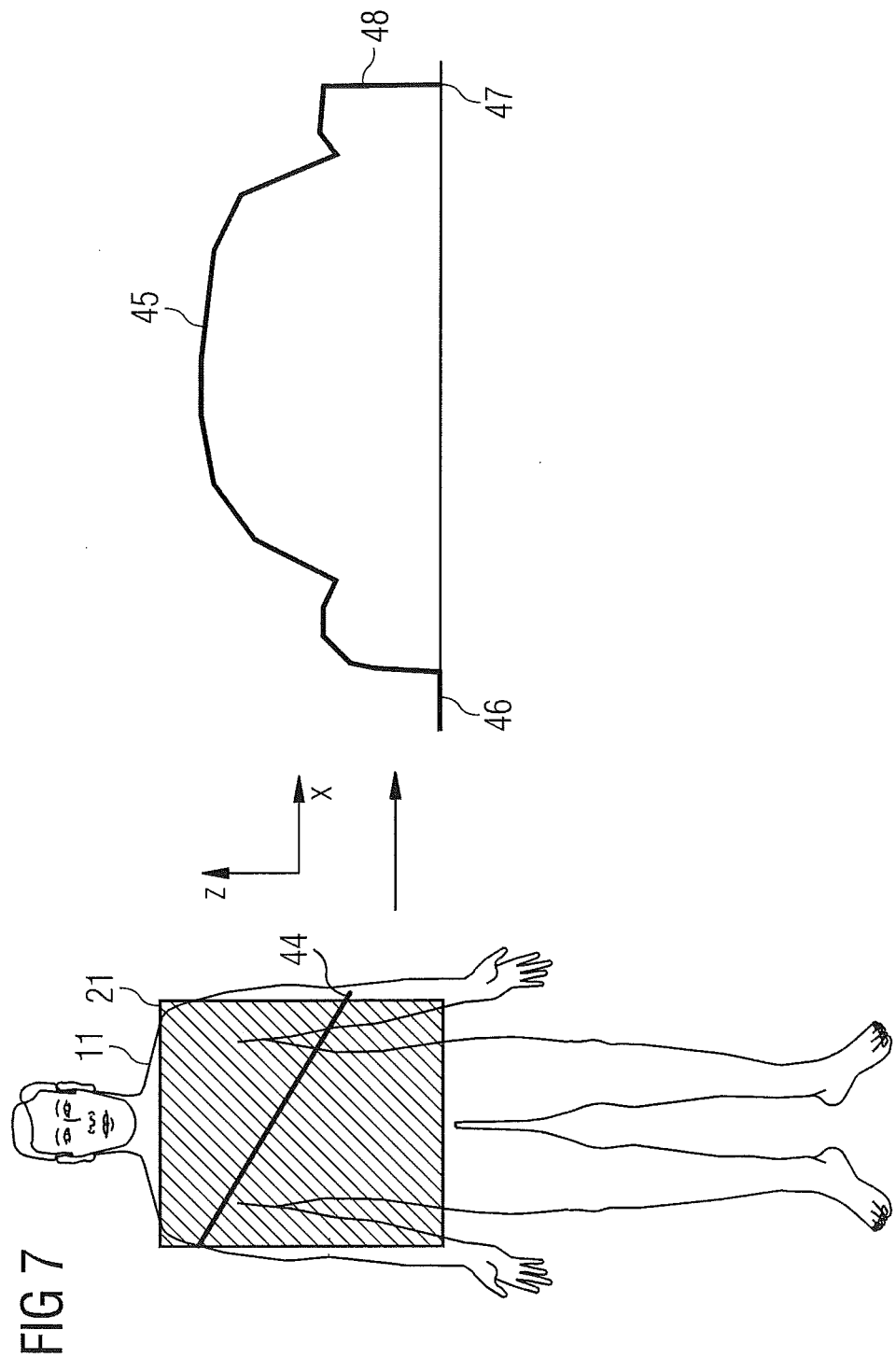

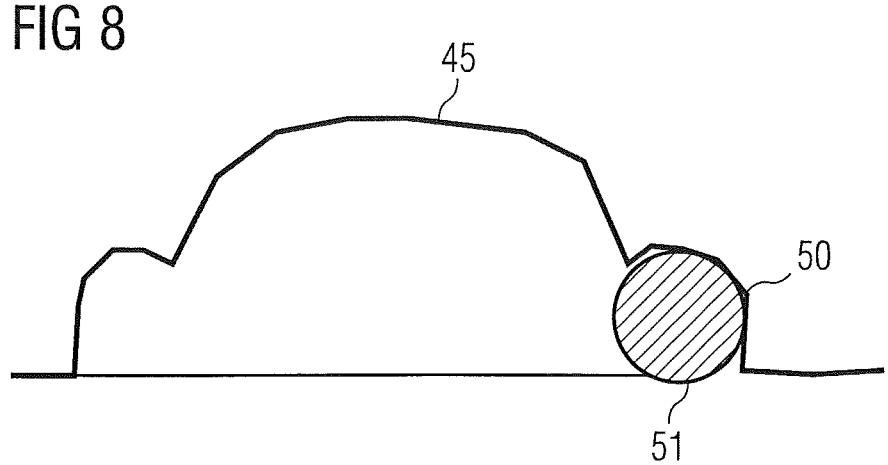
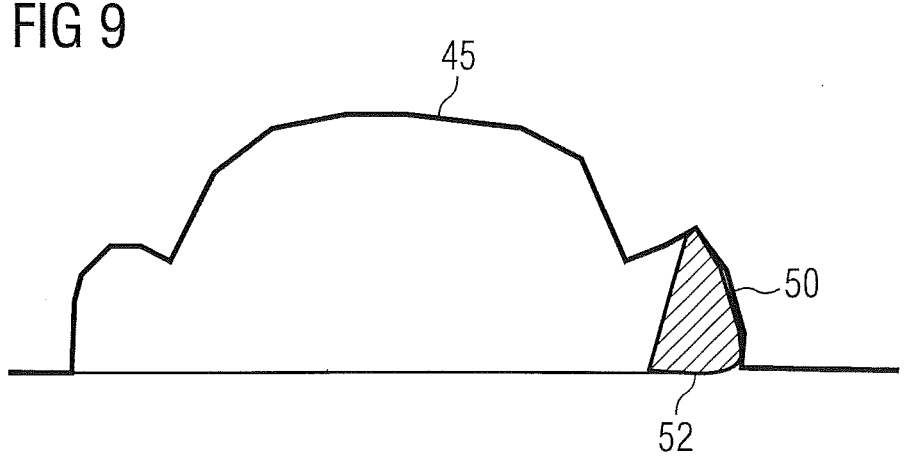

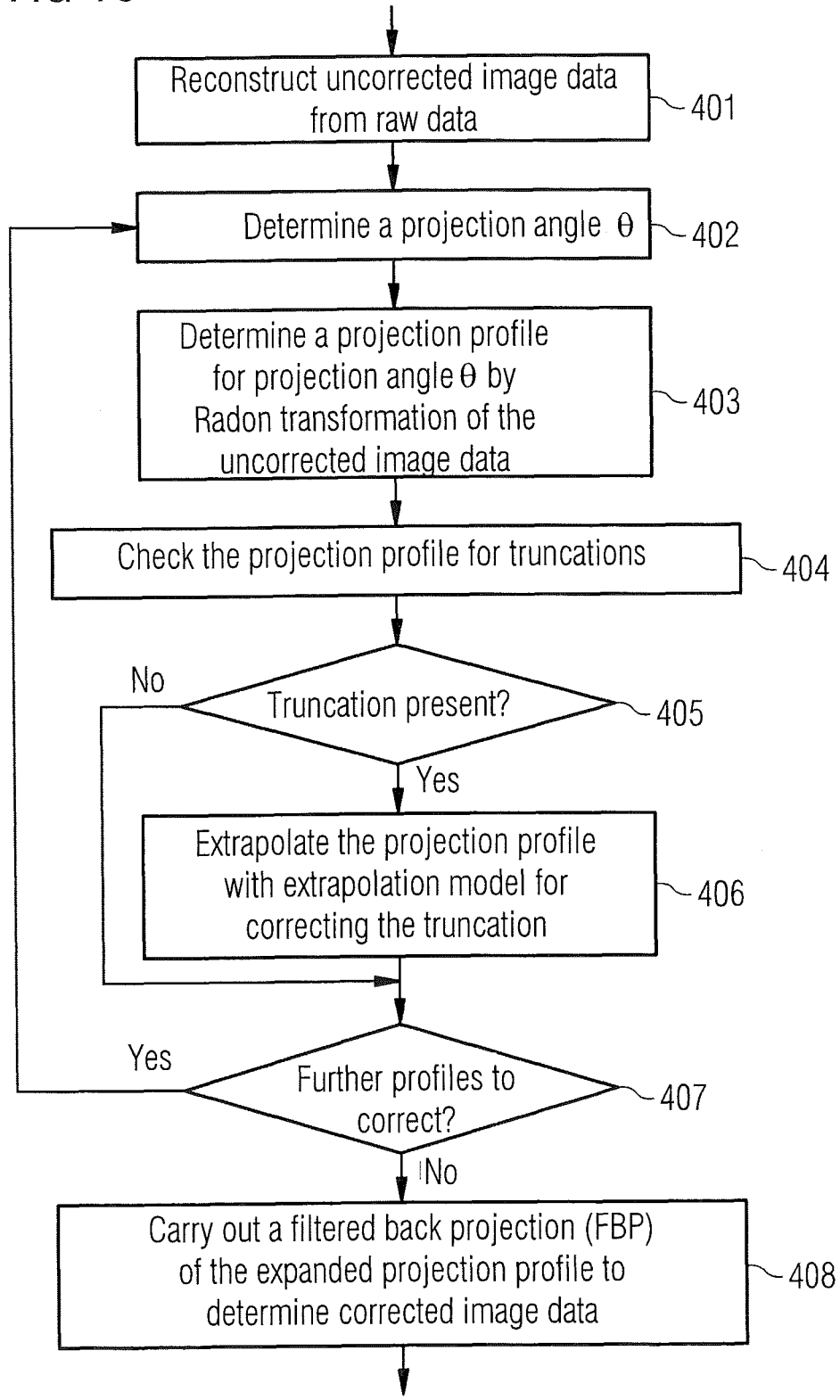

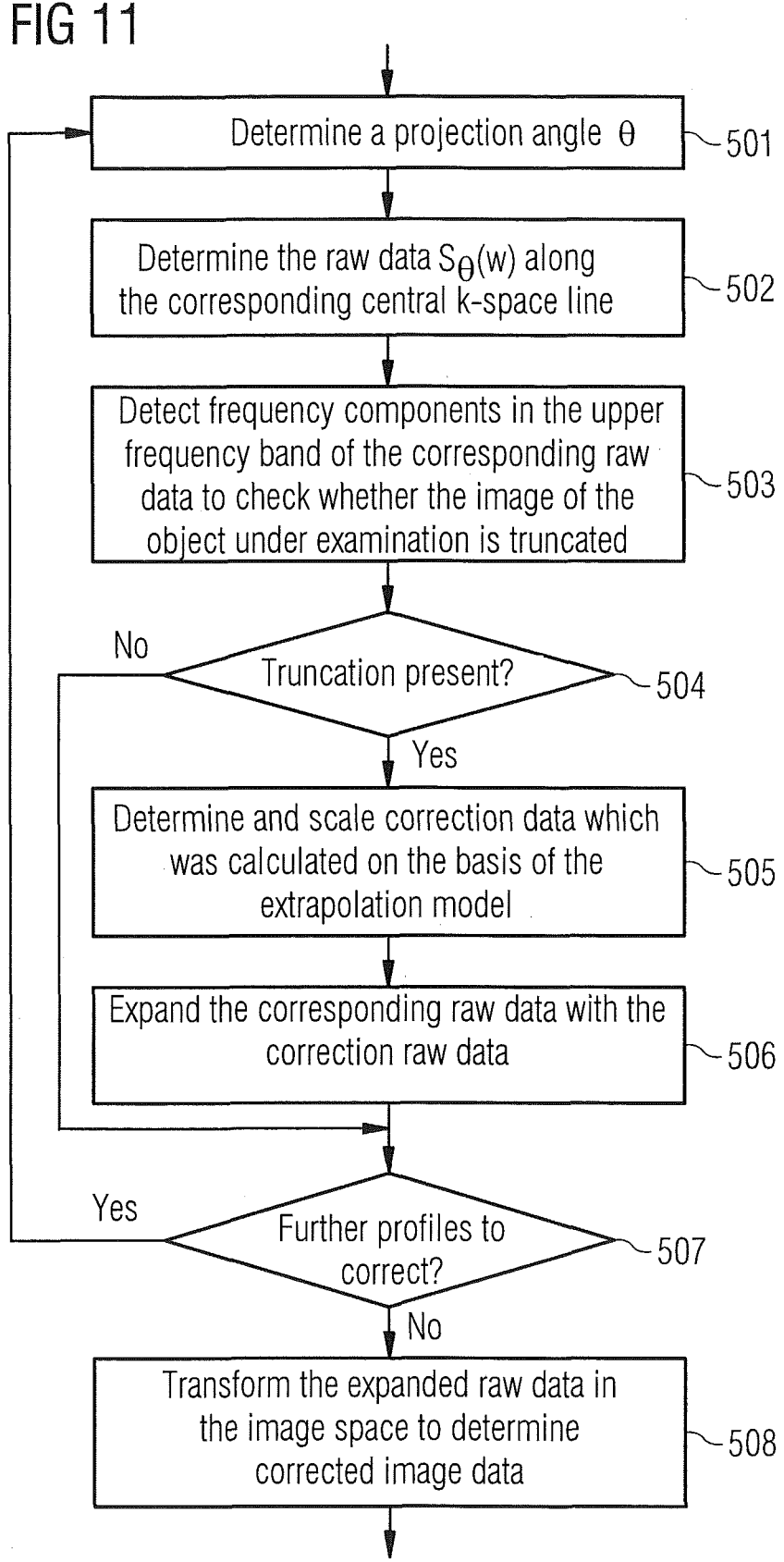

CORRECTION OF TRUNCATIONS IN MR IMAGING

PRIORITY STATEMENT

The present application hereby claims priority under 35 U.S.C. §119 on German patent application number DE 10 2009 048 302.0 filed Oct. 5, 2009, the entire contents of which are hereby incorporated herein by reference.

FIELD

At least one embodiment of the present invention generally relates to a method for correction of truncations of an image of an object under examination in the reconstruction of image data from magnetic resonance raw data and/or to a magnetic resonance system.

BACKGROUND

Magnetic resonance tomography (MRT) is a modern method of examination with makes possible high-resolution imaging of slices of a person to be examined. Images of different types of tissue, especially also soft tissue, can be recorded with this method with high contrast. To expand the high-resolution image data with a functional imaging, MRT can be combined with Positron Emission Tomography (PET). Image data recorded with a combined MR-PET system and can thus deliver locally highly-resolved image information as well as functional information from the same region of the person under examination. In PET a person under examination has a weakly radioactive substance administered to them, the distribution of which in the organism is made visible by the decay of positrons which are emitted by the radionuclide. In such cases coincident decay events are detected and evaluated with annular detectors. On their passage through the material, such as the body of the person under examination for example, the photons arising during the decay can be absorbed, with the probability of absorption depending on the distance that the photons travel through the body of the person under examination. Accordingly a correction of these signals in relation to the attenuation by anatomical structures which are also located in the beam path is necessary in PET. For a combined MR-PET system such an absorption correction can be undertaken on the basis of recorded MR image data since this allows the position and contour of the person under examination to be reconstructed.

However the field of view (FoV) is limited in MR imaging, to 50 to 55 cm in the trans-axial direction for example. In particular a $B_0$-homogeneity reducing at the edges of the field of view and a non-linearity of the magnetic field gradients in the outer areas of the field of view are responsible for the restriction of the field of view. This often leads to truncated or cut-off anatomical structures, such as truncated arms and shoulders for example, in the outer areas of the field of view. This problem is exacerbated in the examination of larger and overweight patients. In actual MR imaging the truncation of the structures does not represent any problem if the anatomical structures to be differentiated are located within the field of view. However for an absorption correction of PET data based on recorded MR image data, the truncation of the structures leads to significant errors. Parts of the body lying outside the field of view of the MR imaging can have a significant influence on the overall attenuation of the measured PET signal. Such problems arise in equal measure for radiation therapy which is planned on the basis of the MR image data.

With conventional methods this problem would typically be resolved by correcting of missing parts of the MR image data by means of an external body contour which has been extracted from uncorrected PET image data. This method is described in greater detail in Delso et al, "Impact of limited MR field-of-view in simultaneous PET/MR acquisition", J. Nucl. Med. Meeting Abstracts, 2008; 49: 162P.". Other approaches derive the missing image information of the body contour directly from PET raw data by means of different reconstruction methods. The missing information is provided in such cases exclusively on the basis of the PET raw data. Such methods are typically described in IEEE Trans. Med. Imag., vol. 18, pp. 393-03, 1999, "Simultaneous maximum a posteriori reconstruction of attenuation and activity distributions from emission sinograms" by J. Nuyts, et al, IEEE TRANSACTIONS ON MEDICAL IMAGING, VOL. 19, NO. 5, MAY 2000 451, "Reconstruction of Attenuation Map Using Discrete Consistency Conditions" by Andrei V. Bronnikov, and in IEEE TRANSACTIONS ON NUCLEAR SCIENCE, VOL. 54, NO. 1, February 2007, "Activity and Attenuation Reconstruction of Positron Emission Tomography Using Emission Data Only Via Maximum Likelihood and Iterative Data Refinement", Fabiana Crepaldi et al. However the disadvantage of these methods is that they require an initialization with a suitably selected start value and often converge in the direction of local and not global optima. These methods, since they are also based on PET raw data, must operate with incorrectly absorption-corrected data because of the truncations. Furthermore it is necessary for detectable amounts of the PET tracer to be located in the structures of the person under examination which are truncated in the MR image data, so that a signal is obtained from these structures. Extremities of the person under examination which are primarily affected by the truncation effects often only contain an insufficient amount of the PET tracer however and as a consequence are only shown badly contoured in the PET images. PET image data also as a rule have a significantly smaller local resolution than corresponding MR image data. Accordingly significant errors frequently occur in the correction of truncations based on PET data.

Furthermore there is an atlas and model-based method in which the PET absorption correction is undertaken on the basis of the model of the person under examination. Model or atlas-based methods can however not take account of the naturally occurring variance of body shapes and the actual position of the person under examination.

Other suggestions include the use of additional, external information sources, such as optical systems, ultrasound systems etc. for example. However the disadvantage of these methods is that additional measurement devices are needed and that in addition the person under examination in the MR-PET system is generally covered by local coils or other apparatus, so that detection of the body contour is rendered more difficult. Furthermore such measurement devices can have a disruptive effect on the MR-PET measurements.

Consequently it is desirable reliably to correct or to avoid truncations in MR image data with minimum effort.

SUMMARY

At least one embodiment of the present invention provides an improved correction of truncations which arise as a result of a restricted field of view of an MR system.

In accordance with a first aspect of at least one embodiment of the present invention a method is provided for correction of truncations of an image of an object under examination in the reconstruction of image data from raw data which was recorded with a magnetic resonance system from a field of view of the magnetic resonance system. An object under examination which is located in the field of view of the magnetic resonance system is imaged in the raw data. The image of the object under examination recorded by the raw data is truncated at the edge of the field of view if at least one part of the object under examination is located outside the field of view.

The method of at least one embodiment of comprises the following steps: Determining a number of one-dimensional projections of the imaged field of view in the Radon space from the recorded raw data in order to obtain a projection profile in each case of the imaged object under examination over the field of view; Checking each projection profile for whether the projection profile exhibits a truncation which is caused by the at least one part of the object under examination being located outside the field of view; if the respective checked projection profile exhibits a truncation, expanding the projection profile for correcting the truncation by extrapolating the projection profile in accordance with a predetermined extrapolation model in the area in which it features the truncation; and reconstruction of image data based on the expanded projection profiles in which the truncation of the image of the object under examination is corrected.

The truncations of the image of the object under examination are consequently corrected in the reconstructed image data. This essentially corresponds to an expansion of the field of view. The use of the projection profiles enables the truncations to be detected and compensated for in a simple manner. The Radon space in which the projection profiles are present is, like the image space in the local space, in which it is possible to go from raw data or k-space by way of a Fourier transformation taking into account the central slice theorem or from the image space by means of a Radon (or projection) transformation. No PET raw data is needed for the correction which can only provide images of the extremities with distortions or badly contoured. The method also manages without any additional external information. The image data and raw data can also be referred to as MR image or raw data.

In accordance with an embodiment of the present invention the raw data can be recorded by scanning the k-space with a prespecified scanning sequence. The number of one-dimensional projections in the image space can be determined in each case by a transformation, especially a Fourier transformation, of the raw data along a predetermined line in the k-space. This enables the projection profiles of the imaged object under examination to be determined in a simple manner. The raw data along a k-space line can also be referred to as a k-space profile or Fourier slice.

A predetermined line in the k-space can in this case correspond to a central k-space line in each case extending from a center of the k-space in a radial direction. The raw data can for example be measured directly along the central line or be interpolated along this line. In accordance with the central slice theorem the one-dimensional projections can thus be determined in a simple manner.

In an embodiment of the method the k-space is scanned row-by-row. This can also be referred to as Cartesian scanning. Once again the central k-space lines can be used as predetermined lines, however the individual k-space rows can also be used.

In another form of embodiment the k-space is sampled with radial scanning, in which the raw data is recorded along a number of the central k-space lines. Thus no interpolation of central k-space lines is needed to determine the projection profile.

The radial scanning can be undertaken along a spherical trajectory for imaging a three-dimensional field of view or along a circular trajectory, for example within a specific slice, for imaging a two-dimensional field of view. The central k-space lines along which the k-space is sampled thus typically end on the said spherical or circular shape. Thus an efficient scanning of the k-space and a good contrast in the corresponding image data is ensured.

In a further form of embodiment of the inventive method uncorrected image data is determined from the raw data by a transformation in which the image of the object under examination is truncated, with the number of one-dimensional projection being determined by projecting the uncorrected image data along predetermined directions of projection. If the raw data typically shows a slice of the object under examination, corresponding projections can be determined in the slice plane. If the raw data maps a three-dimensional field of view, then for example slices in the three-dimensional image can be determined in which corresponding one-dimensional projections are then determined. The projection can for example be undertaken by means of a Radon transformation. Thus the projection profiles can be determined in an efficient manner in the Radon space.

Checking whether the projection profile features a truncation can be undertaken on the basis of profile values at the edges of the projection profile. For example it is established that projection profile exhibits a truncation at an edge if a profile value of the projection profile at the edge lies above a prespecified threshold value or if the gradient of the profile value curve of the projection profile at the edge lies above or below a prespecified threshold value. The profile values in such cases typically correspond to image intensities of the projection. Thus for example a steep fall in the profile value curve which can be detected by means of the gradient can give an indication of the truncation. The threshold value can also be at zero, so that with a profile value at the edge of the projection profile of not equal to zero a truncation is established. Such a method makes possible a simple and reliable detection of truncations.

The extrapolation model can be predetermined for example on the basis of a profile value and/or of a gradient of a profile value curve at an edge of the projection profile at which the projection profile is extrapolated. A sensible extrapolation can thus be insured. In particular the type of the truncated structure can be estimated from these parameters, so that a suitable extrapolation model is able to be predetermined on the basis of the parameters.

The extrapolation model can typically comprise a parabola-shaped curve, a circle segment or a Gaussian curve for extrapolating the projection profile. Thus the missing or truncated projection values can be approximated. Thus in agreement with the profile value and the slope of the profile at the edge to be extrapolated, the extrapolation model can be adapted precisely to the projection profile by scaling, adapting the position and adapting the slope, for example via the peak width at half height of the respective curve.

The extrapolation model can also include a profile curve which was determined using a cylindrical or a parabolic water model. These profile curves can typically be calculated by means of computer-simulated projection values for a water cylinder. The adaptation at the edge to be extrapolated can again be undertaken by scaling and shifting the corresponding profile curves.

For example the projection profile is extrapolated with an extrapolation model in the form of a Gaussian curve if the projection profile at the edge to be expanded has a concave curvature and with an extrapolation model in the form of a profile curve determined on the basis of a water cylinder model if the projection profile at the edge to the expanded has a convex curvature.

In accordance with a form of embodiment of the inventive method the reconstruction of the image data includes the following steps: Transforming the expanded projection profile in the k-space in which the raw data is present; and transforming the expanded k-space data thus obtained in the image space for reconstruction of the image data. Thus an effective correction of the raw data in the k-space is undertaken so that the corrected image data can be determined in a simple manner by a Fourier transformation. The corrected image data can in such cases be determined either exclusively from expanded k-space data or from a combination of expanded k-space data with original, uncorrected k-space data.

In another form of embodiment the image data is reconstructed by a filtered back projection of the expanded projection profiles. Thus the projection profiles can be transformed in a simple manner from the Radon space into the image space. Non-truncated and thus uncorrected projection profiles can naturally also be taken into account in the filtered back projection. Thus corrected image data can be directly determined on the basis of the expanded projection profiles.

It is likewise conceivable for the reconstruction of the corrected image data to be undertaken using a Cartesian reconstruction or a regridding.

In the raw data a slice of the object under examination can be imaged, with truncations of the image of the object under examination being corrected in the plane of the imaged slice. Thus for example a number of raw data records which each show a specific slice can be recorded so that corrected three-dimensional image data can be obtained from the corresponding corrected slice image data.

It is however also possible for a three-dimensional field of view to be imaged in the raw data. By determining k-space profiles on the basis of the raw data the one-dimensional projection profiles can also be determined in a simple manner with a three-dimensional scanning of the k-space. A three-dimensional field of view can be recorded and imaged for example by a volume excitation. In such cases it is conceivable to employ parallel imaging methods such as SMASH or GRAPPA for example. Central k-space profiles can be determined using interpolation or regridding methods. If the object under examination is moved in a direction of movement through the field of view of the magnetic resonance system, in order to record a number of raw data sets, preferably the truncations are corrected which lie in the direction perpendicular to the axis of movement outside the field of view.

In accordance with a form of embodiment the magnetic resonance system is a combined MR-PET system which is configured for recording PET data from an area under examination of the MR-PET system, with the method further including an absorption correction of recorded PET data based on the reconstructed image data. Thus a precise and reliable absorption correction of the PET data is made possible even if parts of the object under examination, such as the extremities of a person under examination for example, are located outside the field of view of the MR measurements.

In accordance with a further aspect of at least one embodiment of the present invention a corresponding method for correcting truncations of an image of an object under examination is provided, with the method carrying out the detection of the truncations and the correction of the truncations in the k-space. The method comprises checking the raw data for whether the image of the object under examination is truncated in the raw data by detecting frequency components in the raw data which were generated by a truncation of the image in the image space and if the raw data maps a truncation of the image, expanding the raw data by adding correction raw data which was determined by transformation of an extrapolation model in the k-space, with the extrapolation model including a profile curve for extrapolating a truncated projection profile in the Radon space. Subsequently image data is reconstructed by transforming the unexpanded raw data in the image space.

The method in accordance with this further aspect of at least one embodiment has the advantage that the raw data is checked and expanded directly in the k-space without a transformation in the image space or Radon space and a back transformation having to take place. In this case it is once again possible to carry out the checking and expansion on corresponding k-space profiles which typically correspond to pre-specified central lines in the k-space. For checking the raw data for a truncation, frequency components are typically detected in the form of sinc-like oscillations above a specific threshold frequency in the raw data, which are caused by the sharp edge in a truncation present in the image space.

In accordance with a form of embodiment the correction raw data is scaled before it is added, with the amplitude of the correction data being scaled to adapt the extrapolation model to the profile values of the image at the point of the truncation, and with the frequency of the correction raw data being scaled to adapt the extrapolation model to the location of the truncation. Thus a suitable scaling function allows the correction data in the k-space to be adapted such that the truncation correction carried out in this way is undertaken at the correct point of the corresponding profile in the Radon space.

The extrapolation model can typically be one of the extrapolation models given above.

In another form of embodiment the correction raw data includes the spectrum of a cylindrical or a parabolic water model. These spectrums can in their turn typically be determined by computer simulation of a k-space spectrum to be expected on receiving MR raw data from the corresponding models. Thus a precise and suitable correction of the raw data in the k-space is insured.

In the method a number of k-space profiles are determined for example along central k-space lines, with the checking and expansion being undertaken by checking and expanding the number of k-space profiles. In this case central k-space profiles are preferably determined by interpolation for example.

The method in accordance with the further aspect of at least one embodiment of the present invention can likewise include features which have been described previously with reference to the first aspect, such as in relation to the different sampling methods for the k-space for example.

In accordance with a further aspect of at least one embodiment of at least one embodiment of the present invention a magnetic resonance system is provided which is embodied for the correction of truncations of an image of an object under examination in the reconstruction of image data from raw data. The magnetic resonance system features a recording unit which is designed for recording raw data from a field of view of the magnetic resonance system as well as a control unit which is designed to control the recording unit for recording the raw data if an object under examination is located in the field of view, with the object under examination being mapped in the raw data and with the image of the object under examination captured by the raw data being truncated at the edge of the field of view if at least one part of the object under examination is located outside the field of view. Furthermore the magnetic resonance system comprises a processing unit which is designed to determine a number of one-dimensional projections of the imaged field of view in the Radon space from the recorded a raw data in order to obtain in each case a projection profile of the imaged object under examination over the field of view; checking each projection profile as to whether the projection profile exhibits a truncation which is caused by the at least one part of the object under examination being located outside the field of view; if the respective checked projection profile exhibits a truncation, expanding the projection profile for correcting the truncation by the projection profile being extrapolated in accordance with a predetermined extrapolation model in the area in which it exhibits the truncation; and reconstructing image data based on the expanded projection profiles in which the truncation of the image of the object under examination is corrected.

With the magnetic resonance system designed in this way the same advantages can be obtained as were previously described in relation to at least one embodiment of the inventive method.

In accordance with a form of embodiment the magnetic resonance system is a combined MR-PET system and comprises a PET recording unit for recording PET data. In this form of embodiment the processing unit is designed to carry out an absorption correction of recorded PET data based on the reconstructed image data. With this combined MR-PET system, both MR data with an enlarged field of view can be determined and also corrections of recorded PET data can be reliably carried out. In particular the PET data does not have to be corrected on the basis of uncorrected or wrongly corrected PET raw data.

The magnetic resonance system can additionally be designed to carry out one of the previously described methods, especially in accordance with the first aspect of at least one embodiment of the present invention.

In accordance with a further aspect of at least one embodiment of the present invention the processing unit of the magnetic resonance system is designed for carrying out the expansion of the raw data in the k-space. In particular the processor unit is designed to check the raw data for whether the image of the object under examination is truncated in the raw data, by detecting frequency components in the raw data which can be caused by a truncation of the image in the image space; if the raw data exhibits a truncation of the image, expanding the raw data by adding correction raw data which was determined by transformation of an extrapolation model in the k-space, with the extrapolation model including a profile curve for extrapolating a truncated projection profile in the Radon space; and reconstructing image data by transforming the expanded raw data in the image space.

Accordingly the processing unit typically does not initially have to transform a raw data profile present in the k-space in the Radon space and also carry out a back transformation of the expanded profile. The advantages previously described in relation to a second aspect of at least one embodiment of the present invention can also be achieved with the magnetic resonance system.

The magnetic resonance system can likewise be a combined MR-PET system with a corresponding PET recording unit, with the processing unit again able to undertake a correction of recorded PET data on the basis of the reconstructed MR image data or MR raw data. The magnetic resonance system can also be designed for carrying out a method previously described in relation to the second aspect of at least one embodiment of the present invention.

In accordance with a further aspect of at least one embodiment of the present invention a computer program product with a computer program is provided which executes one of the previously described methods when executed in a computer system. The computer program product can also be referred to as a program for a data processing system.

Furthermore an electrically-readable data carrier with electronically-readable control information stored thereon is provided which is embodied such that it executes one of the previously described methods when the data carrier is used in a computer system.

Naturally the features of the previously described aspects and forms of embodiment of the present invention can be combined.

BRIEF DESCRIPTION OF THE DRAWINGS

Embodiments of the invention will be explained in greater detail below with reference to the enclosed drawings.

FIG. 5 is a flow diagram of a form of embodiment of the inventive method which can be executed at step 200 of FIG. 2.

FIG. 7 shows a one-dimensional projection profile in the image space which exhibits a truncation at the edge of the corresponding field of view.

FIG. 8 illustrates the extrapolation of a truncated projection profile with an extrapolation model in accordance with a form of embodiment of the present invention.

FIG. 9 illustrates the extrapolation of a truncated projection profile with an extrapolation model in accordance with a form of embodiment of the present invention.

FIG. 10 is a flow diagram of a form of embodiment of the inventive method which can be executed at step 200 of FIG. 2.

FIG. 11 is a flow diagram of a form of embodiment of the inventive method which can be executed at step 200 of FIG. 2.

DETAILED DESCRIPTION OF THE EXAMPLE EMBODIMENTS

Figure 1:
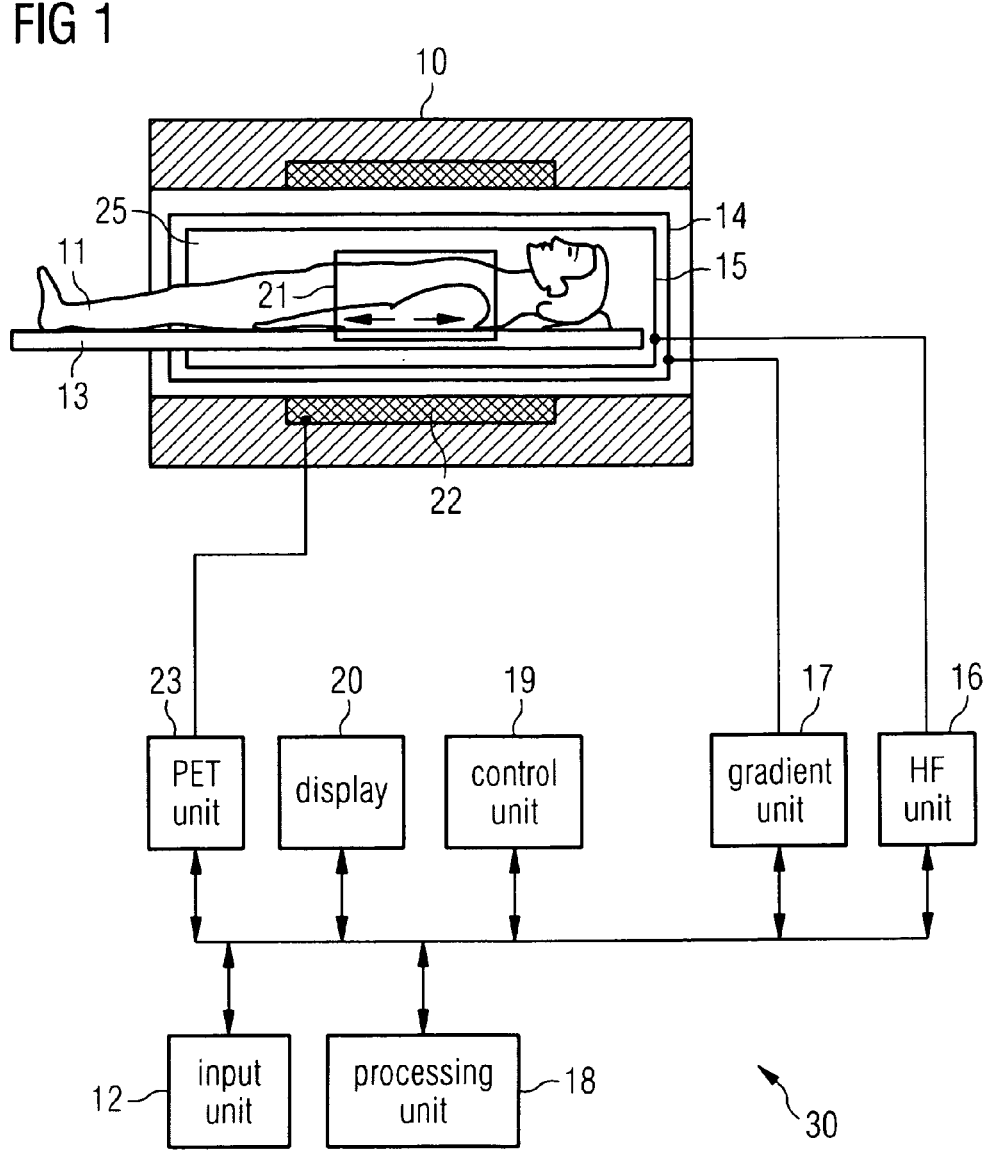
FIG. 1 shows a schematic diagram of a magnetic resonance system in accordance with a form of embodiment of the present invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic block diagram of a magnetic resonance (MR) system in accordance with a form of embodiment of the present invention which is likewise configured for recording positron emission tomography (PET) data and can thus be referred to as a combined MR-PET system.

With the MR system 30 the correction of truncations of an image of an object under examination, i.e. a person under examination 11 can be executed in the reconstruction of image data from raw data recorded by the MR system 30. Such an MR system features a magnet 10 for creating a polarization field $B_0$ auf. The person under examination in 11 is pushed on the table 13 into the magnets, as is shown schematically by the arrows. The MR system also features a gradient system 14 for generating magnetic field gradients which are used for imaging and local encoding. To excite the polarization produced in the main magnetic fields a high frequency coil arrangement 15 is provided which radiates a high-frequency field into the person under examination 11 to deflect the magnetization from the position of equilibrium. To control the magnetic field gradients a gradient unit 17 is provided and to control the irradiated HF pulses an HF unit 16 is provided.

The $B_0$ magnetic only has a sufficient homogeneity for MR imaging in a specific area. Consequently only a restricted field of view 21 can be imaged in the recording of MR signals. Furthermore the size of the field of view is restricted by the non-linearity of the magnetic field gradients in the outer areas of the field of view. In the transaxial direction, i.e. in the direction perpendicular to the plane of the figure, the field a view 21 can for example have a size of 50 to 55 cm. The size of the field of view in this case is smaller than the size of the area under examination 25 of the MR system 30. Consequently the field of view 21, especially with large or overweight persons under examination, does not cover the whole body of the person under examination in the transaxial direction, so that extremities, for example arms 6 shoulders, are truncated or cut off in the image. Parts of the person under examination 11 which lie outside the field of view 21 are not taken into account in the recording of the magnetic resonance signals, so that these parts are not imaged in the corresponding MR raw data. The field of view thus generally refers to the area which is imaged with a specific recording sequence or with the recording sequence used. Depending on the imaging sequence used, the field of view 21 can thus have a different size, with truncations regularly occurring even with a maximum field of view. In the longitudinal direction (z) the field of view can be increased by the person under examination 11 being moved by means of the patient bed 13 through the field of view 21. At right angles to the longitudinal direction (z) and to the transaxial direction (x), i.e. in the y-direction, truncations can of course likewise occur which can be corrected by the MR system 30.

The components used for recording MR signals, such as the HF coil arrangement 15, the HF unit 16, the gradient system 14 and the gradient unit 17 for example, can be grouped together and referred to as the recording unit. The control unit controls the magnetic resonance systems centrally, such as the execution of a prespecified imaging MR sequence. The imaging sequence to be executed can typically be selected with the input unit 12. Control information, e.g. imaging parameters, as well as reconstructed image data, can be shown on the display 20.

To record raw data, control unit 19 controls the scanning of the k-space, with this being filled with raw data by the recording of MR signals at different created phases and if necessary frequency encoding gradients. Thus the k-space can for example be sampled with Cartesian sampling, with a k-space row corresponding to the recording of a frequency-encoded signal at a specific phase encoding. Of course a phase encoding can also be undertaken in two or three dimensions so that a three-dimensional k-space is sampled.

As well as the row-by-row sampling of the k-space, a radial sampling is especially advantageous. In this case the raw data is recorded along k-space lines which extend through the k-space center. Such sampling of the k-space can be achieved by corresponding switching of the gradient system 14 by means of the gradient unit 17. Such sampling of the k-space is illustrated as an example in FIG. 4 for a two-dimensional layer. The k-space layer 40 contains the central k-space lines 41 which pass through the origin 42 of the k-space and along which the k-space is sampled.

For the recording of the raw data the excitation pulse should be designed so that all protons of the entire object in the field of view are excited so that the raw data for the central k-space line to be recorded corresponds to a projection of image data as well as possible. In the signal recording along the radial readout direction it is advantageous to select a sufficiently high oversampling in order to avoid aliasing artifacts, which can be caused by the folding-in of truncated objects.

Naturally the MR system 30 can also be designed to carry out other MR imaging methods known to the person skilled in the art. Thus the magnetic resonance signals can be recorded with local body coils or view sharing or other methods can be used which repeatedly partly sample the k-space, for recording the raw data, such as SMASH, GRAPPA or similar.

Recorded raw data can both include a 3D data record and also one or more sampled slices which were recorded for example by way of a slice selection gradient.

The recorded raw data is processed in the processor unit 18 of the MR system 30. Truncations of the image of the person under examination 11 recorded in the raw data which are produced as a result of the restricted field of view 21 are corrected by processing unit 18. The correction of the truncations can be undertaken in such cases either in the Radon space or in the k-space. Processor unit 18 can for example determine k-space profiles (or slices or Fourier slices) and correct these directly or in the Radon space. It is also possible for processing unit 18 to correct specific projection profiles on the basis of image data (e.g. by way of Radon transformation). The correction is undertaken, as described in detail below, by way of an extrapolation model by expanding the truncated profile. In particular processor unit 18 can be embodied for executing one of the methods described in greater detail below.

MR system 30 also features a PET system, with a PET unit 23 being provided for controlling the PET system 22. PET system 22 comprises a PET detector which can be designed for example as an annular detector with a plurality of scintillation detector units. In this case the PET system 22 records coincidences between each two detectors lying precisely opposite one another. Based on the temporal and spatial distribution of the registered coincident decay events, the spatial distribution of the corresponding radio pharmaceutical in the inside of the body of the person under examination 11 can be estimated. Because of the high magnetic fields which are used in the recording of magnetic resonance signals semiconductor detectors are preferably used in the PET system 22, such as avalanche photodiodes for example. To record PET data the control unit 19 can control the PET unit so that a combined PET-MRT measurement is made possible.

The corresponding PET image data is reconstructed in the processor unit 18 from the recorded PET data. In such cases an absorption correction of the PET data by way of a μ-map is undertaken, which is created based on the corrected MR image data with the processor unit 18. Since the truncations of the image of the person under examination 11 are corrected in the MR image data, the μ-map can reflect the absorption behavior of the person under examination 11 highly accurately, so that an improved absorption correction is achieved.

MR system 30 can of course feature further components which are known from conventional MR systems. The general functioning of an MR system is known to the person skilled in the art, so that a more detailed description of the general components will not be provided here.

Figure 2:
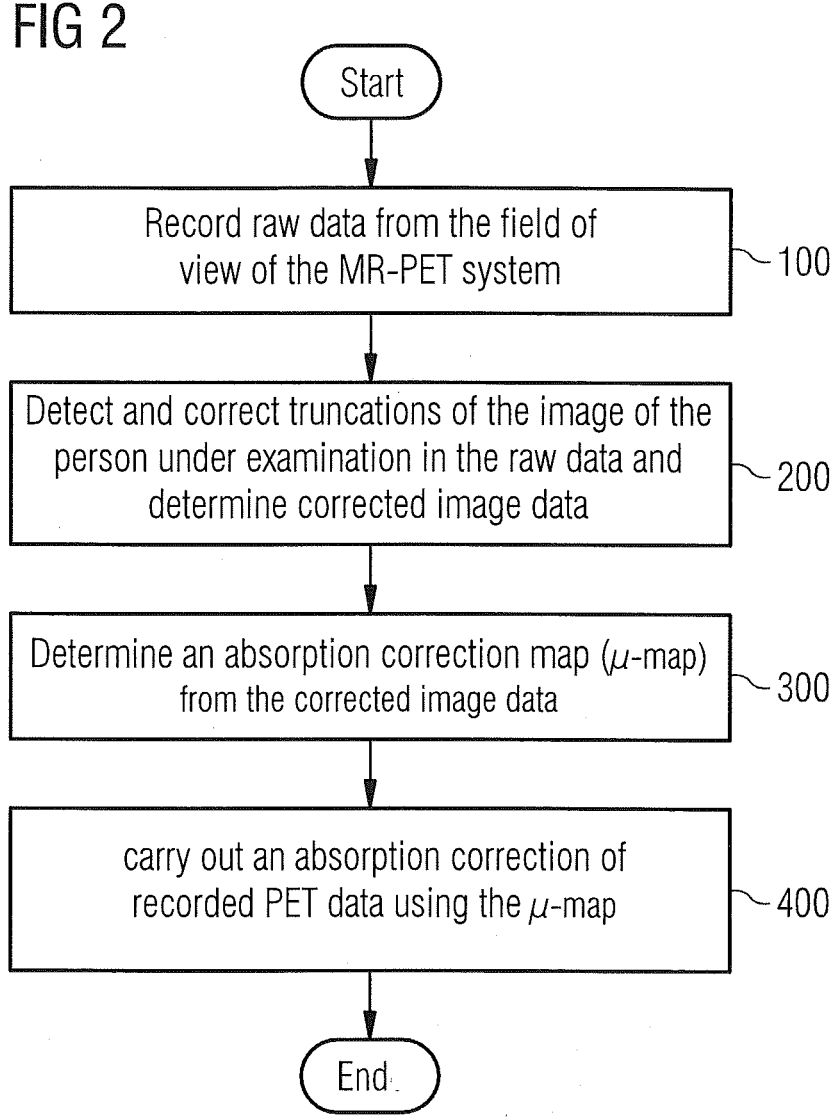
FIG. 2 shows a flow diagram of a form of embodiment of the inventive method.
Figure 3:
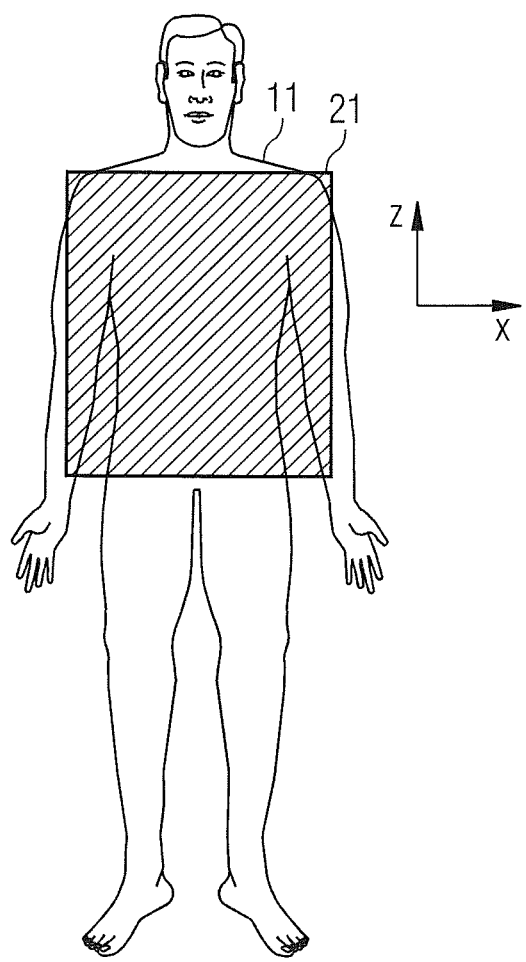
FIG. 3 shows the MR field of view imaged by the MR-PET system.
Figure 4:
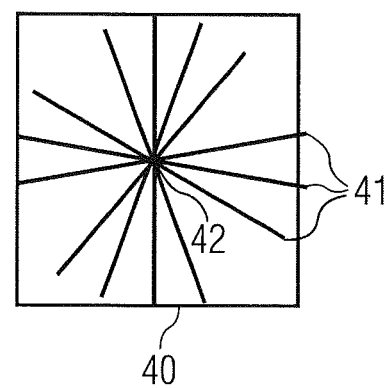
FIG. 4 illustrates schematically a radial sampling of the k-space corresponding to the field of view.

FIG. 2 shows a form of embodiment of the inventive method which can be carried out by means of the MR system 30. In a first step 100 raw data is recorded from the field of view of the MR-PET system. This is shown by way of example in FIG. 3, which shows a contour of the person under examination as well as the field of view 21 of the MR system 30. In the transaxial direction x the field of view 21 does not capture all areas of the person under examination 11, so that in the present example the arms of the person under examination are only recorded partly in the image. As previously mentioned, the person under examination 11 can be moved in the longitudinal direction z by means of the support table, so that areas of the person under examination which extend beyond the field of view 21 in this direction can be imaged in subsequent measurements. The recording of the raw data is illustrated in FIG. 4, with reference sign 40 identifying the field of view 21 transformed into the k-space. This can be sampled as shown radiantly along central k-space lines 41, however a row-by row sampling is likewise conceivable.

Once again referring to FIG. 2, in a next step 200 truncations of the image of the person under examination in the raw data are detected and corrected and the corrected image data is determined. Method step 200 is described in greater detail below with reference to FIGS. 5, 10 and 11.

From the corrected image data an absorption correction map (μ-map) is determined in step 300, with which in step 400 an absorption correction of recorded PET data is carried out. The determination of a μ-map based on MR image data of a person under examination as well as carrying out an absorption correction are known to the person skilled in the art so that they will not be discussed in greater detail here.

In FIG. 5 step 200 in accordance with a form of embodiment of the inventive method is described in more detail. The method here is based on the idea that a number of different projections of the imaged object under examination are determined with different angles of projection so that a projection profile is obtained in each case. If a truncation is detected in the profile, the corresponding profile is expanded beyond the field of view predetermined by the MR system. After the processing of all predetermined projections an image reconstruction is carried out which calculates the correct image on the basis of the extrapolated data and thereby effectively leads to an enlarged field of view.

The projection angles θ, which are used for determining the projection profile can be defined in different ways. They can for example the pre-specified by a predetermined recording sequence to record the raw data, e.g. with a radial sampling of the k-space) or they can be defined as a function of the desired accuracy and resolution of the correction.

Figure 6A:
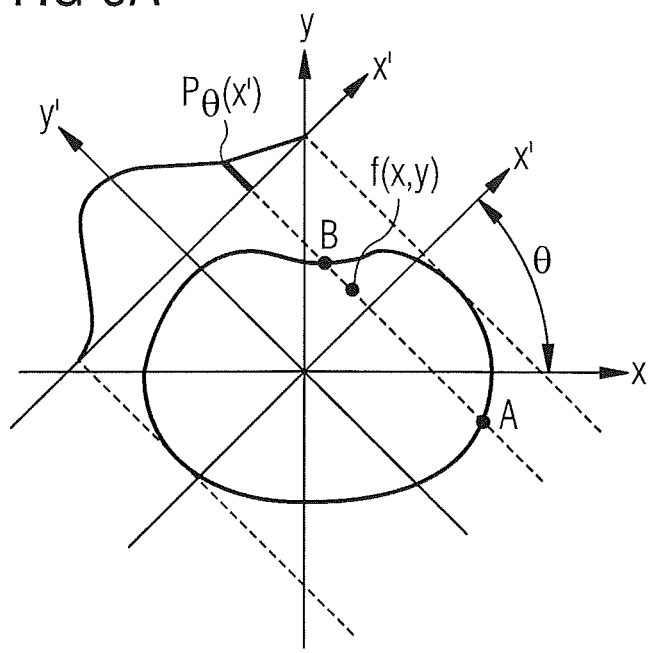
FIGS. 6*a* and 6*b* are schematic diagrams which illustrate the central slice theorem.
Figure 6B:
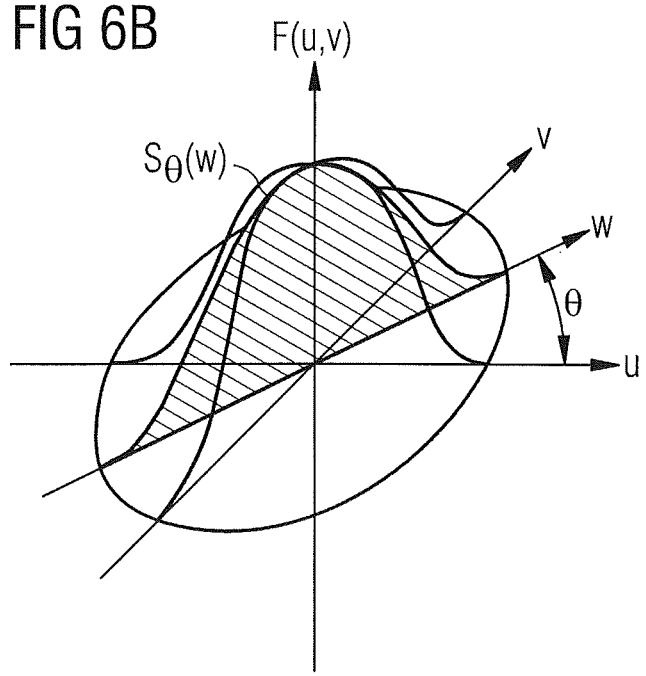

Accordingly, in step 301, a projection angle θ is first determined for which the projection profile is to be corrected. For this projection angle, in step 302 raw data $S_\theta(w)$ is determined along the corresponding central k-space line. This is shown by way of example in FIG. 6*b*. FIG. 6*b* shows the k-space which corresponds to the transformed field of view, with the k-space being shown in two dimensions with the axes u and v. By pre-specifying the projection angle θ the central k-space line w is determined, which extends through the origin of the k-space.

With a radial sampling of the k-space these types of central k-space line can be sampled directly, so that the raw data for this k-space line can be used directly. For the sampling of a slice for example, a circular trajectory can be employed in which a predetermined number of k-space lines end with a pre-specified angle θ on a circular trajectory in the k-space. Equally, for a three-dimensional sampling, a spherical trajectory can be employed in which the corresponding central k-space lines to be sampled end on the surface of the sphere of the trajectory in the k-space. In the three-dimensional case the direction of the lines to be sampled can be predetermined for example by two angles (azimuth angle and polar angle). In FIG. 6b F(u, v) designates the k-space value or recorded signal value for the respective k-space point. The course of the k-space values along an axis in the k-space, such as the central k-space line w for example, can also be referred to as the k-space profile.

Again referring to FIG. 5, in a next step 303 the projection profile $P_\theta(x')$ is calculated for the specific k-space profile $S_\theta(w)$ by inverse Fourier transformation. To determine the projection profile at the projection angle θ the central slice theorem is applied. In accordance with this theorem the Fourier transformation of a k-space slice at an angle θ (or of a k-space profile) corresponds to a projection in the Radon space $P_\theta(x')$ at the projection angle θ, since the projection profile can be calculated in accordance with $$P_\theta(x') = \int_{y'=-\infty}^{+\infty} f(x, y) ds \qquad (1)$$
$$= \int_{-\infty}^{+\infty} \int_{-\infty}^{+\infty} f(x, y) \delta(x\cos\theta + y\sin\theta - x') dx dy.$$

As illustrated in FIG. 6b the k-space profile can be determined in accordance with $$S_\theta(w) = \text{slice}\{F(u,v)\}. \qquad (2)$$

Accordingly the projection profile can be determined in accordance with $$P_\theta(x') = \mathfrak{J}^{-1}\{S_\theta(w)\}, \qquad (3)$$

with $\mathfrak{J}^{-1}$ designating the inverse Fourier transformation. The central slice theorem is illustrated in greater detail in FIG. 6a. The profile values of the projection profile $P_\theta(x')$ are produced by summation of the values in the image space f(x,y) along the projection lines which are at right angles to the profile axis x', with the profile axis x' featuring the projection angle θ to the x axis. This means that it is therefore possible to determine the projection profile for the predetermined angle θ in a simple manner as soon as the corresponding k-space data is available. In particular no summation of image values has to be carried out, the Fourier transformation of a central k-space slice or profile is simply sufficient. As already previously described in detail, the k-space cannot only the sampled radially, but also row-by-row, or with another generally used sampling method. In this case it is advantageous to determine the raw data for a central k-space line or a central k-space profile by interpolation, regridding or by a similar method. This method allows k-space profiles to be calculated with great accuracy. Such methods are known to the person skilled in the art, so that no further description of the method will be provided here.

After the execution of the inverse one-dimensional Fourier transformation for determining the one-dimensional projection profile, the projection profile is checked for truncations in step 304. As illustrated in FIG. 7, the truncations can be detected on the basis of the profile values at the edges of the projection profile.

On the left-hand side of FIG. 7 an example shows a person under examination as well as the field of view of the MR system. Furthermore the drawing includes a projection profile 44 by way of example. If the person under examination is not fully captured by the field of view 21, the profile values at the corresponding edge of the projection profile, which actually correspond to the sum of the image intensity values in the projection direction, are not equal to zero. This is illustrated for another projection profile 4 in more detail on the right-hand side of FIG. 7. At the left edge of the projection profile 4 the profile values fall back to a value of almost zero, so that it can be deduced from this that on the corresponding side of the field of view there is no truncation of the image of the person under examination 11. If the profile values are not equal to zero as at the right edge 47 of the profile 45, a truncation 48 can be deduced. For example a truncation 48 is deduced if the profile value at the edge of the profile lies above a predetermined threshold value. It is also possible for the projection profile to fall steeply at the edge if a truncation is present, so that the profile value curve features a comparatively high gradient at the edge of the profile. If the amount of the gradient at the edge of the profile lies above a predetermined threshold value, the presence of a truncation can likewise be deduced.

If it is established in decision step 305 that a truncation is present, in step 306 the projection profile is extrapolated with an extrapolation model for correcting the truncation. In this case the field of view is essentially expanded by adding additional profile values which are selected in accordance with the extrapolation model for a meaningful completion of the profile. For this purpose the number of data points (samples) of the profile can also be increased if necessary. In this case a plurality of possible extrapolation models can be used to obtain a meaningful completion of the profile.

FIG. 8 shows an example of the expansion of the projection profile by extrapolation by way of profile values determined on the basis of a water cylinder model of specific profile values. For correction of truncations of the extremities in particular, such as the arms for example, the use of a water cylinder model is advantageous since the corresponding profile values can be well emulated by this model. The missing profile values are created in such cases by a computer-simulated MR imaging of the water cylinder. The projection profile 45 is expanded by profile values 50 generated in this way.

The extrapolation model can likewise include profile values which have been determined on the basis of a parabolic water model, as illustrated in FIG. 9. The parabolic water model consists in this case of a volume filled with water delimited by a plane and an extruded parabola. In their turn profile values are again calculated by computer simulation for the parabolic water model 52 with which the projection profile 45 is expanded.

Further extrapolation models can of course also be used. The missing profile values can for example be approximated by a Gaussian curve, a circle arc segment or a parabola-shaped curve or segment. It is also possible to include other information sources in the extrapolation model as well, which can serve to expand the projection profile. Examples of this are information from optical, ultrasound or other systems or facilities, information from uncorrected PET image data, or similar.

The extrapolation model can be adapted in such cases by scaling and moving the position to the edge of the projection profile to be expanded, so that a seamless and if necessary smooth transition between the projection profile and the expanded profile values is produced. In particular the profile values and the profile gradient at the edge of the projection profile 45 to be expanded can be taken into account for the adaptation. Based on these properties of the projection profile the extrapolation model to be used can likewise be selected. For example a water cylinder model can then be used to correct the truncation if the gradient at the right edge of the projection profile is negative (convex curvature). If the gradient is positive (concave curvature), the projection profile is extrapolated with a Gaussian curve. A corresponding method can be used for the left profile edge.

A simple but meaningful expansion of the projection profiles can be undertaken with such a method so that the truncation of the profile is corrected in a suitable manner. The correction operator $\xi$ produces the corrected projection profile for $$P^*_\theta(x') = \xi\{P_\theta(x')\}. \tag{4}$$

The expanded projection profile $P^*_\theta$ is transformed in step 307 by way of a Fourier transformation back into the k-space.

$$S^*_\theta(w) = \Im\{P^*_\theta(x')\}. \tag{5}$$

Thus a new corrected set $F^*(u,v)$ of corrected raw data present in the k-space can be created. Profiles which do not exhibit any truncation can likewise be added to the corrected raw data set. On the other hand it is likewise possible to expand the original raw data with the corrected k-space profiles. In step 308 the method branches back to step 301 if projection profiles for further projection angles are to be checked and if necessary expanded.

After the projection profiles for the prespecified projection angles $\theta$ have been checked and corrected, a transformation of the expanded raw data in the image space for determining corrected image data is undertaken in step 309. In the case of a two-dimensional k-space this can be done by way of a two-dimensional Fourier transformation in accordance with $$f^*(x,y) = \Im^{-1}\{F^*(u,v)\} \tag{6}.$$

In the corrected image data $f^*(x,y)$ the truncations of the image of the person under examination 11 are corrected. With the corrected image data the contour of the person under examination can now be determined in a definitive area and used accordingly for creating an absorption correction map.

Naturally other types of determining the corrected image data are also possible. Thus for example a back transformation of the extrapolated projection profiles into the k-space can be omitted and the corrected image data can be determined directly on the basis of the extrapolated projection profiles by a filtered back projection. In such cases one moves from the Radon space in which the extrapolated projection profiles are present directly into the image space. Other methods, such as regridding or a Cartesian reconstruction for example, are likewise applicable for determining the corrected image data.

Further variations of the method are described below with reference to FIGS. 10 and 11, with the above remarks being equally valid for the methods described below, especially in respect of the detection of truncations and the expansion of the projection profiles.

For the method of FIG. 10 which can likewise be executed in place of step 200 of FIG. 2, the truncations are essentially corrected in the image space. For this purpose, in step 401 initially uncorrected image data $f(x,y)$ are reconstructed from the recorded raw data $F(u,v)$ for example by two-dimensional Fourier transformation. This means that after the sampling of the k-space by means of any given imaging sequence, the MR reconstruction is undertaken without taking account of the truncations. Accordingly the uncorrected image data exhibits truncation artifacts which will be corrected afterwards. In step 402 first of all, as in the method in accordance with FIG. 5, a projection angle $\theta$ is specified which, as explained with reference to FIG. 6, defines the projection profile to the corrected. For this projection angle, in step 403 a projection profile in the Radon space is determined by way of a Radon transformation of the uncorrected image data.

$$P_0(x') = \Re\text{adon}\{f(x,y,\theta)\}. \tag{7}$$

The Radon transformation corresponds to the projection of the image values on the axis x' defined by the projection angle $\theta$. Subsequently the truncations are detected and corrected essentially in the same way as in the method in accordance with FIG. 5. In step 404 the projection profile is checked for truncations and if truncations are established in decision step 405, in step 406 the projection profile is extrapolated with the extrapolation model for correcting the truncation:

$$P^*_\theta(x') = \xi\{P_\theta(x')\}. \tag{8}$$

A back transformation of the extrapolated projection profile in the k-space is not necessary with the method, but can be undertaken however.

The correction is carried out for the other predetermined projection angles $\theta$ until, in step 407 there are no further profiles to be corrected. Subsequently, in step 408, a filtered back projection (FBP) of the expanded projection profiles is carried out to determine corrected image data.

$$f^*(x,y) = \Im_{BP}\{P^*_\theta(x')\}. \tag{9}$$

As described previously with reference to FIG. 5, further methods for reconstruction of the corrected image data can also be employed.

For the method illustrated in FIG. 11, the truncations are detected and corrected in the k-space. This avoids a backwards and forwards transformation between the k-space and the Radon space or image space. Time-consuming and complex operations such as Fourier transformations can be saved in this way.

The method used is based especially on the known properties of the Fourier transformation and the commutativity of Fourier and addition operators. A truncation of a function in the image space leads to sinc-shaped oscillations and vibrations in the corresponding Fourier spectrum. To detect truncations in the projection profiles, in the present method sinc oscillations are detected in the corresponding k-space profiles. This initially avoids the first inverse Fourier transformation in the Radon space for determining the projection profile. By exploiting the exchangeability of Fourier and addition operators in this case, the second Fourier transformation back into the k-space is also avoided. With this method pre-calculated Fourier spectrums of the said extrapolation model are used for correction and a suitably-scaled version of the spectrums is added directly to the k-space profile. In this way the field of view is expanded by direct correction of truncations in the k-space by using efficient scaling and addition operations. In this case a scaling profile in the k-space can bring about the necessary amplitude adaptation and also the position adaptation of the extrapolation model in the Radon space.

In step 501 the projection angle $\theta$ is first determined once again. For this projection angle, in step 502 raw data $S_\theta(w)$ is determined along the corresponding central k-space line, i.e. the k-space profile or the k-space slice $$S_\theta(w) = \text{slice}\{F(u,v)\} \tag{10}$$

is extracted from the raw data. Frequency components in the upper frequency band of the k-space profile are detected to check whether the image of the object under examination is truncated. This can be done by unfolding the corresponding signal curve for example with a Wiener filter, a sinus cordinalis (sinc) decomposition or wavelet decomposition, with the high frequency components created by the truncation able to the split off in the k-space. Other filters can also be used to detect frequency components at the edges of the spectrum of the k-space profile which originate from a truncation.

If a truncation is present, in step 505 correction data which was calculated on the basis of the extrapolation model is determined and scaled. As regards the extrapolation model, the reader is referred to the remarks given above. The correction raw data essentially corresponds to a Fourier transformation of the respective extrapolation model and thereby to a k-space profile. It will be scaled in an appropriate manner in order to expand the truncated parts of the image of the person under examination in the checked k-space profile. In this case on the one hand the amplitude of the correction raw data can be scaled in order to adapt the model to the corresponding edge of the profile to be expanded and a frequency scaling of the correction raw data can be undertaken in order to position the corresponding extrapolation model at the right position in the image space. The scalings can be carried out directly on the correction or data without a transformation being necessary into the Radon or image space. To this end for example the parameters determined in the wavelet decomposition for detecting the upper frequency components can be used which are actually predetermined by the position and amplitude of the truncation. To check the scaling the high frequency components in the k-space can be considered in their turn, which should have disappeared with a suitable expansion of the profile for correction of the truncation. As an alternative a check in the Radon space or the image space is possible, with the reader once again being referred to the above remarks in respect of expanding the profile in the Radon space.

After suitable scaling in step 506 the k-space profile is expanded with the correction data. This can be done in accordance with the equation $$S^*_\theta(w) = \xi\{S_\theta(w)\} \tag{11},$$

with $\xi$ once again representing a correction operator here and $S^*_0(w)$ identifying the corrected k-space profile for the projection angle $\theta$. The expansion can typically be undertaken by a simple addition of the raw data of the k-space profile and the correction raw data. If in step 507 profiles are to be corrected for further predetermined projection angles, a branch is made back to step 501. If this is not the case, then corrected image data f*(x,y) can be calculated (step 208) from the expanded raw data by way of the transformation $$f^*(x,y) = \Im^{-1}\{F^*(u,v)\} \tag{12}$$

In the corrected image data determined in this way the truncations of the image of the person under examination or of the object under examination are corrected.

Naturally further variations of the methods previously described are conceivable. For example it is possible to restrict the expansion of the field of view, i.e. the correction of the truncations to one spatial direction. This can be of importance especially for the recording of the MR raw data in a number of stages. Thus the expansion can for example be restricted to just the x or the y direction. It should also be pointed out that the features of the forms of embodiment previously described can be combined.

A method for correction of truncations which are caused by a restricted field of view is provided with the present invention, with the method not being reliant on external data sources such as PET data, optical cameras and the like for example. This information can however be integrated additionally into the method. The method can be implemented easily and leads to a significant improvement of the absorption correction of recorded PET data.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

10 Magnet
11 Person under examination
12 Operating unit
13 Patient table
14 Gradient system
15 High-frequency coil arrangement
16 HF unit
17 Gradient unit
18 Processor unit
19 Control unit
20 Display
21 Field of view
22 PET system
23 PET unit
25 Area under examination
30 Magnetic resonance system
40 Field of view transformed in k-space
41 Central k-space lines
44 Projection profile
45 Projection profile
46 Left edge of the projection profile
47 Right edge of the projection profile
48 Truncation
50 Expanded profile values
51 Water cylinder model
52 Parabolic water model
100-400 Method steps
301-309 Method steps
401-408 Method steps
501-508 Method steps

What is claimed is:

1. A method for correction of truncations of an image of an object under examination in the reconstruction of image data from raw data which has been recorded with a magnetic resonance system from a field of view of the magnetic resonance system, wherein the object under examination, located in the field of view of the magnetic resonance system, is imaged in the raw data and the image of the object under examination, recorded by the raw data, is truncated at the edge of the field of view such that at least one part of the object under examination is located outside the field of view, the method comprising:

determining a number of one-dimensional projections of the imaged field of view in the Radon space from the recorded raw data in order to obtain, for each one dimensional projection, a projection profile of the imaged object under examination over the field of view;

checking each projection profile to determine whether the projection profile exhibits a truncation which is caused by the at least one part of the object under examination being located outside the field of view;

expanding, upon determining that a respective checked projection profile exhibits a truncation, the respective projection profile by correcting the truncation by the projection profile being extrapolated in accordance with an extrapolation model in an area in which it exhibits the truncation; and reconstructing image data based on the expanded projection profiles, in which the truncation of the image of the object under examination is corrected.

2. The method as claimed in claim 1, wherein the raw data is recorded by sampling the k-space with a sampling sequence, with the number of one-dimensional projections in the Radon space, each being determined by a transformation of the raw data along a line in the k-space.

3. The method as claimed in claim 2, wherein the line in the k-space corresponds to a central k-space line in each case which extends from a center of the k-space in the radial direction.

4. The method as claimed in claim 3, wherein the k-space is sampled with a radial sampling in which the raw data is recorded along a number of the central k-space lines.

5. The method as claimed in claim 4, wherein the radial sampling is undertaken along a spherical trajectory for mapping a three-dimensional field of view or along a circular trajectory for mapping a two-dimensional field of view.

6. The method as claimed in claim 3, wherein the k-space is sampled row by row.

7. The method as claimed in claim 2, wherein the k-space is sampled row by row.

8. The method as claimed in claim 1, wherein uncorrected image data is determined from the raw data by a transformation, in which the image of the object under examination is truncated, with the number of one-dimensional projections being determined by projecting the uncorrected image data in prespecified projection directions.

9. The method as claimed in claim 8, wherein the projection is undertaken by way of a Radon transformation.

10. The method as claimed in claim 1, wherein the checking of whether the projection profile exhibits a truncation is undertaken on the basis of profile values at the edges of the projection profile.

11. The method as claimed in claim 10, wherein it is established that the projection profile exhibits a truncation at one edge if a profile value of the projection profile at the edge lies above a prespecified threshold value or if a gradient of the profile value curve of the projection profile at the edge lies above or below a threshold value.

12. The method as claimed in claim 1, wherein the extrapolation model is determined on the basis of at least one of a profile value and of a gradient of a profile value curve at the edge of the projection profile at which the projection profile is extrapolated.

13. The method as claimed in claim 1, wherein the extrapolation model comprises a parabola-shaped curve, a circle segment or a Gaussian curve for extrapolating the projection profile.

14. The method as claimed in claim 1, wherein the extrapolation model comprises a profile curve which has been specified using a cylindrical or parabolic water model.

15. The method as claimed in claim 1, wherein the reconstruction of the image data comprises:
transforming the expanded projection profile in the k-space in which the raw data is present, and
transforming the expanded k-space data obtained in this way into the image space for reconstruction of the image data.

16. The method as claimed in claim 1, wherein the image data is reconstructed by a filtered back projection of the expanded projection profiles.

17. The method as claimed in claim 1, wherein the corrected image data is reconstructed by a Cartesian reconstruction or a regridding.

18. The method as claimed in claim 1, wherein a slice of the object under examination is imaged in the raw data, with truncations of the image of the object under examination being corrected in the plane of the imaged slice.

19. The method as claimed in claim 1, wherein a three-dimensional field of view is imaged in the raw data.

20. The method as claimed in claim 1, wherein the magnetic resonance system is a combined MR-PET system which is configured for recording PET data from an area under examination of the MR-PET system, the method further comprising absorbing correction of recorded PET data based on the reconstructed image data.

21. A non-transitory computer program product with a computer program which, when executed in a computer system having a processor, the processor carries out the method in accordance with claim 1.

22. An electronically-readable non-transitory data carrier with electronically-readable control information stored thereon, which is designed to, when the data carrier is used in a processor system having a processor, execute, using the processor, the method as claimed in claim 1.

23. A non-transitory computer readable medium including program segments for, when executed on a computer device having a processor, causing the processor of the computer device to implement the method of claim 1.

24. A method for correcting truncations of an image of an object under examination in the reconstruction of image data from raw data which was recorded with a magnetic resonance system from a field of view of the magnetic resonance system and is present in k-space, an object under examination which is located in the field of view of the magnetic resonance system being imaged in the raw data, and the image of the object under examination mapped by the raw data being truncated at the edge of the field of view such that at least a part of the object under examination is located outside the field of view, the method comprising:
checking the raw data to determine whether the image of the object under examination is truncated in the raw data by detecting frequency components in the raw data which are caused by a truncation of the image in the image space;
expanding, upon determining that the raw data exhibit a truncation of the image, the raw data by adding correction raw data which has been determined by transformation of an extrapolation model in the k-space, with an extrapolation model including a profile curve for extrapolating a truncated projection profile in the Radon space; and
reconstructing image data by transforming the expanded raw data in the image space.

25. The method as claimed in claim 24, wherein the correction raw data is scaled before being added, with the amplitude of the correction raw data being scaled to adapt the extrapolation model to the profile values of the image at the point of the truncation, and with the frequency of the correction raw data being scaled to adapt the extrapolation model to the location of the truncation.

26. The method as claimed in claim 25, wherein the extrapolation model comprises a parabola-shaped curve, a circle segment or a Gaussian curve for extrapolating the projection profile.

27. The method as claimed in claim 25, wherein the extrapolation model comprises a profile curve which has been specified using a cylindrical or parabolic water model.

28. The method as claimed in claim 24, wherein the extrapolation model comprises a parabola-shaped curve, a circle segment or a Gaussian curve for extrapolating the projection profile.

29. The method as claimed in claim 24, wherein the correction raw data comprises the spectrum of a cylindrical or parabolic water model.

30. The method as claimed in claim 24, wherein a number of k-space profiles are determined from the raw data along central k-space lines, with the checking and expansion being undertaken by checking and expanding the number of k-space profiles.

31. The method as claimed in claim 24, wherein the extrapolation model comprises a profile curve which has been specified using a cylindrical or parabolic water model.

32. A non-transitory computer readable medium including program segments for, when executed on a computer device having a processor, causing the processor of the computer device to implement the method of claim 24.

33. A magnetic resonance system equipped for correction of truncations of an image of an object under examination in the reconstruction of image data from raw data, comprising:
a recording unit to record raw data from a field of view of the magnetic resonance system;
a control unit to control the recording unit for recording the raw data upon an object under examination being located in the field of view, with the object under examination being mapped in the raw data and with the image recorded by the raw data of the object under examination being truncated at the edge of the field of view upon at least one part of the object under examination being located outside the field of view;
a processing unit, designed to determine a number of one-dimensional projections of the imaged field of view in the Radon space from the recorded raw data, in order to obtain a projection profile of the imaged object under examination over the field of view; to check each projection profile to determine whether the projection profile exhibits a truncation which is caused by the at least one part of the object under examination being located outside the field of view; to expand, upon the check to the respective projection profile determining that the respective projection profile exhibits a truncation, the respective projection profile to correct the truncation by the projection profile being extrapolated in accordance with an extrapolation model in the area in which it exhibits the truncation; and to reconstruct image data based on the expanded projection profiles in which the truncation of the image of the object under examination is corrected.

34. The magnetic resonance system as claimed in claim 33, wherein the magnetic resonance system is a combined MR-PET system and comprises a PET recording unit for recording PET data, the processing unit being designed to carry out an absorption correction of recorded PET data based on the reconstructed image data.

35. The magnetic resonance system as claimed in claim 34, wherein the raw data is recorded by sampling the k-space with a sampling sequence, with the number of one-dimensional projections in the Radon space, each being determined by a transformation of the raw data along a line in the k-space.

36. The magnetic resonance system as claimed in claim 33, wherein the raw data is recorded by sampling the k-space with a sampling sequence, with the number of one-dimensional projections in the Radon space, each being determined by a transformation of the raw data along a line in the k-space.

37. A magnetic resonance system which is embodied for correction of truncations of an image of an object under examination in reconstruction of image data from raw data which is present in a k-space, comprising:

a recording unit to record raw data from a field of view of the magnetic resonance system;

a control unit to control the recording unit for recording the raw data upon an object under examination being located in the field of view, with the object under examination being mapped in the raw data and with the image captured by the raw data of the object under examination being truncated at the edge of the field of view upon at least one part of the object under examination being located outside the field of view; and a processor unit to check the raw data as to whether the image of the object under examination is truncated in the raw data by detecting frequency components in the raw data which can be caused by a truncation of the image in the image space; to, upon determining that the raw data exhibits a truncation of the image, expand the raw data by adding correction raw data which has been determined by transformation of an extrapolation model in the k-space, with the extrapolation model comprising a profile curve for extrapolating a truncated projection profile in the Radon space; and to reconstruct image data by transforming the expanded raw data in the image space.

38. The magnetic resonance system as claimed in claimed 37, wherein the magnetic resonance system is a combined MR-PET system and comprises a PET recording unit for recording PET data.

39. The magnetic resonance system as claimed in claim 38, wherein the processing unit is designed to carry out an absorption correction of recorded PET data based on the reconstructed image data.

* * * * *